(12) United States Patent
Ehlert et al.

(10) Patent No.: US 10,325,470 B2
(45) Date of Patent: Jun. 18, 2019

(54) SYSTEM FOR MONITORING HEALTH STATUS OF A PERSON WITHIN AN ENCLOSED AREA

(71) Applicant: CITRIX SYSTEMS, INC., Fort Lauderdale, FL (US)

(72) Inventors: Brian Jeffrey Ehlert, Woodinville, WA (US); Jiayin Tian, Woodinville, WA (US); Christopher Coy Fife, Sammamish, WA (US)

(73) Assignee: CITRIX SYSTEMS, INC., Fort Lauderdale, FL (US)

( * ) Notice: Subject to any disclaimer, the term of this patent is extended or adjusted under 35 U.S.C. 154(b) by 0 days.

(21) Appl. No.: 15/715,686

(22) Filed: Sep. 26, 2017

(65) Prior Publication Data

US 2019/0096218 A1 Mar. 28, 2019

(51) Int. Cl.
*G08B 21/04* (2006.01)
*G16H 40/63* (2018.01)
*G16H 50/30* (2018.01)

(52) U.S. Cl.
CPC ..... *G08B 21/0423* (2013.01); *G08B 21/0446* (2013.01); *G08B 21/0461* (2013.01); *G16H 40/63* (2018.01); *G16H 50/30* (2018.01)

(58) Field of Classification Search
CPC .... G06F 19/32; G06F 19/322; G06F 19/3406; G06F 19/3418; G06F 19/3431; G08B 21/02; G08B 21/0423; G08B 21/0446; G08B 21/0461; G09B 19/00; G09B 19/0092; G16H 40/63; G16H 50/30; A61B 5/0022; A61B 5/1112; A61B 5/1113; A61B 5/6881; A61B 5/6891

USPC .......................................................... 340/521
See application file for complete search history.

(56) References Cited

U.S. PATENT DOCUMENTS

| | | | |
|---|---|---|---|
| 6,796,799 B1 * | 9/2004 | Yoshiike | G06F 19/3418 434/236 |
| 6,840,117 B2 | 1/2005 | Hubbard, Jr. | |
| 9,875,450 B1 * | 1/2018 | Hendrick, III | G16H 50/30 |
| 2005/0131736 A1 * | 6/2005 | Nelson | G06Q 50/22 705/2 |
| 2009/0091458 A1 | 4/2009 | Deutsch | |
| 2009/0315733 A1 * | 12/2009 | Bischoff | G06Q 50/22 340/659 |
| 2010/0063774 A1 * | 3/2010 | Cook | G05B 15/02 702/181 |
| 2010/0145164 A1 * | 6/2010 | Howell | A61B 5/0002 600/301 |

(Continued)

*Primary Examiner* — Quan-Zhen Wang
*Assistant Examiner* — Stephen R Burgdorf
(74) *Attorney, Agent, or Firm* — Allen, Dyer, Doppelt + Gilchrist, PA

(57) ABSTRACT

A system for monitoring a health status of a person within an enclosed area may include a plurality of sensors distributed about the enclosed area. The sensors may be configured to detect respective different types of inputs based upon activity by the person within the enclosed area. The system may also include a computing device cooperating with the sensors to determine when the health status falls below a threshold status level based upon a timing and sequence in which the sensors are activated from the activity of the person within the enclosed area, and generate an alert based upon the health status falling below the threshold status level.

14 Claims, 5 Drawing Sheets

(56) References Cited

U.S. PATENT DOCUMENTS

| | | | | |
|---|---|---|---|---|
| 2014/0104059 A1* | 4/2014 | Tran | .................... | G06F 19/3418 |
| | | | | 340/539.12 |
| 2015/0058275 A1* | 2/2015 | Shimizu | ............... | G08B 21/182 |
| | | | | 706/52 |
| 2015/0220101 A1* | 8/2015 | Aisa | ......................... | G05F 3/04 |
| | | | | 307/31 |
| 2016/0027278 A1* | 1/2016 | McIntosh | ........... | G08B 21/0423 |
| | | | | 715/741 |
| 2016/0345832 A1* | 12/2016 | Pavagada Nagaraja | ..................... | |
| | | | | A61B 5/0022 |
| 2017/0076576 A1* | 3/2017 | Tan | .................... | G06K 9/00771 |
| 2017/0150929 A1* | 6/2017 | Sankai | ................ | A61B 5/7278 |
| 2017/0154516 A1* | 6/2017 | German | ............. | G08B 21/0423 |

* cited by examiner

US 10,325,470 B2

SYSTEM FOR MONITORING HEALTH STATUS OF A PERSON WITHIN AN ENCLOSED AREA

TECHNICAL FIELD

This application generally relates to patient health monitoring systems and related methods.

BACKGROUND

Within elderly care facilities there is a limited number of staff and growing demands to monitor and provide proactive services to patients. Traditionally, patients wear signal buttons which allow them to call for emergency assistance. However, while these can assist in gaining the care a patient needs in an emergency, they may be intrusive and require patient compliance in wearing them.

Furthermore, these types of devices require an affirmative action to be taken on the part of the patient. Yet, in some circumstances the patient is not aware or otherwise able to recognize that he or she needs assistance. Tenants may become unresponsive, ill, or injure themselves, without staff awareness that anything has happened.

Additionally, it is rarely noted when a patient begins slipping into dementia or senility, losing critical time for low cost intervention techniques. There are also privacy regulations that prevent staff from entering tenant rooms without being invited in, or receiving consent from the family, unless an emergency is suspected.

SUMMARY

A system for monitoring a health status of a person within an enclosed area may include a plurality of sensors distributed about the enclosed area. The sensors may be configured to detect respective different types of inputs based upon activity by the person within the enclosed area. The system may also include a computing device cooperating with the sensors to determine when the health status falls below a threshold status level based upon a timing and sequence in which the sensors are activated from the activity of the person within the enclosed area, and generate an alert based upon the health status falling below the threshold status level.

More particularly, at least one of the sensors may be a refrigerator sensor. In accordance with an example implementation, at least one of the other sensors may be a motion sensor, and the computing device may determine that the health status falls below the threshold status level based upon a time between activation of the motion sensor and a subsequent activation of the refrigerator sensor. In accordance with another example implementation, at least one of the other sensors may be a door sensor, and the computing device may determine that the health status falls below the threshold status level based upon a time between activation of the door sensor and a subsequent activation of the refrigerator sensor.

Furthermore, the computing device may generate a baseline from activation of the sensors over time, and determine when the health status falls below the threshold status level further based upon the baseline, for example. In accordance with one example embodiment, none of the sensors are connected to the person. By way of example, one or more of the sensors may comprise Internet of Things (IoT) sensors.

A related method for monitoring a health status of a person within an enclosed area with a computing device may include detecting respective different types of inputs based upon activity by the person within the enclosed area from a plurality of sensors distributed about the enclosed area. The method may further include determining when the health status falls below a threshold status level based upon a timing and sequence in which the sensors are activated from the activity of the person within the enclosed area, and generating an alert based upon the health status falling below the threshold status level.

A related non-transitory computer-readable medium may be for a computing device for monitoring a health status of a person within an enclosed area. The non-transitory computer-readable medium may have computer-executable instructions for causing the computing device to perform steps including detecting respective different types of inputs based upon activity by the person within the enclosed area from a plurality of sensors distributed about the enclosed area, determining when the health status falls below a threshold status level based upon a timing and sequence in which the sensors are activated from the activity of the person within the enclosed area, and generating an alert based upon the health status falling below the threshold status level.

DETAILED DESCRIPTION OF THE EMBODIMENTS

The present description is made with reference to the accompanying drawings, in which exemplary embodiments are shown. However, many different embodiments may be used, and thus the description should not be construed as limited to the particular embodiments set forth herein. Rather, these embodiments are provided so that this disclosure will be thorough and complete. Like numbers refer to like elements throughout, and prime notation is used to indicate similar elements or steps in different embodiments.

Figure 1:
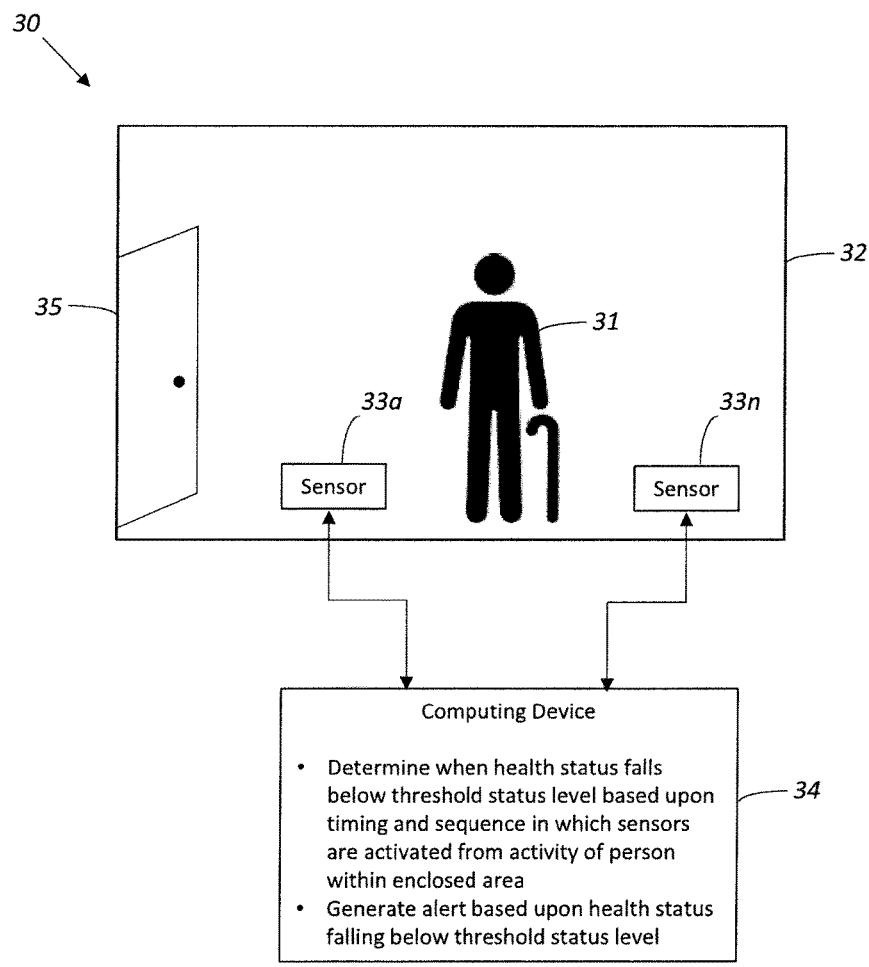
FIG. 1 is a schematic block diagram of an example system for monitoring the health status of a person within an enclosed area in accordance with an example embodiment.
Figure 2:
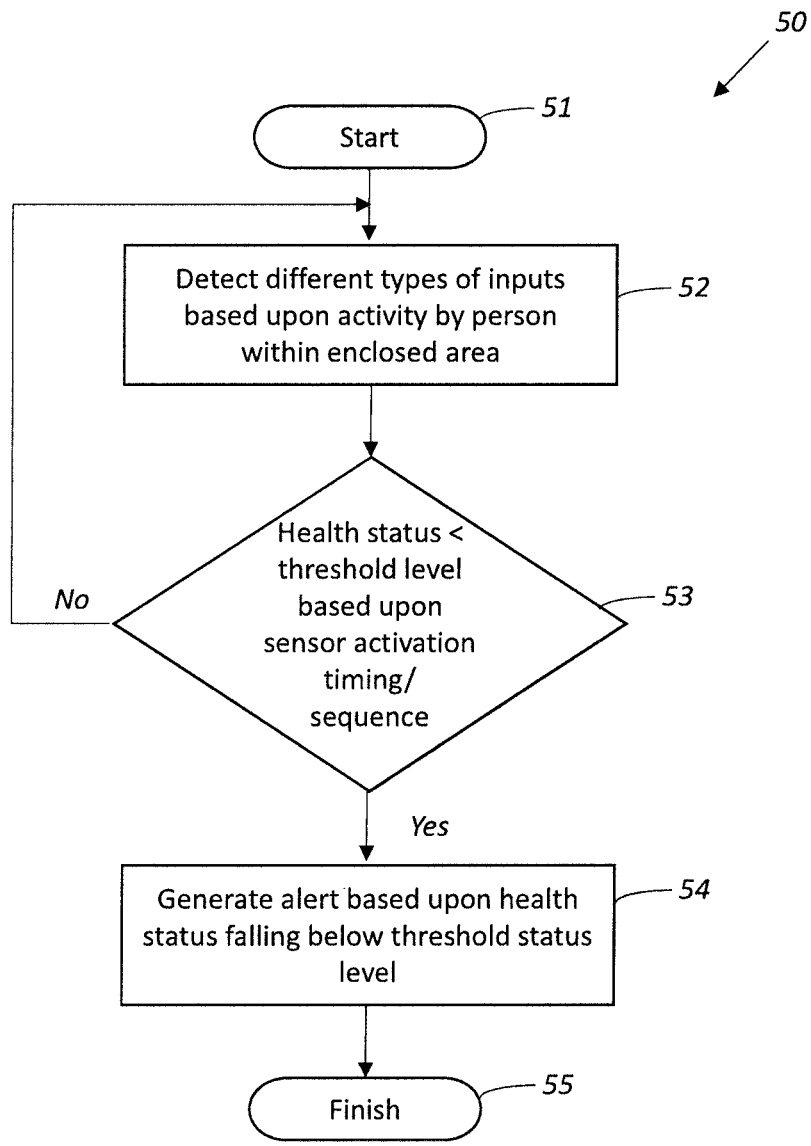
FIGS. 2 and 4 are flow diagrams illustrating method aspects associated with the systems of FIG. 1.

Turning initially to FIG. 1 and the flow diagram 50 of FIG. 2, a system 30 for monitoring the health status of a person 31 within an enclosed area 32 (e.g., a room(s) within a building) and related method aspects are first described. The system 30 illustratively includes a plurality of different sensors 33a-33n distributed about the enclosed area 32. Beginning at Block 51, the sensors 33a-33n may be configured to detect respective different types of inputs based upon activity by the person 31 within the enclosed area 32, at Block 52. Furthermore, the system 30 also illustratively includes a computing device 34 cooperating with the sensors 33a-33n to determine when the health status of the person 31 falls below a threshold status level (Block 53) based upon a timing and sequence in which the sensors are activated from the activity of the person within the enclosed area, and generate an alert based upon the health status falling below the threshold status level, at Block 54. This concludes the method illustrated in FIG. 2 (Block 55).

Generally speaking, the sensors 33a-33n need not be specifically designed for health monitoring applications. That is, the sensors 33a-33n need not be configured to make any determinations about health status on their own. Rather, the computing device 34 may advantageously collect the different inputs or information from the separate sensors 33a-33n, which by themselves do not provide any particular insight into the health status of the person 31, and correlate or aggregate this information to make a determination about the health of the person, as will be discussed further below. The sensors 33a-33n may be hard-wired or wireless sensors in different embodiments, or a combination of both types of sensors. Moreover, in some embodiments the sensors may be Internet of Things (IoT) sensors. Because general purpose sensors 33a-33n may be used in the system 30, this may advantageously allow for greater configurability and lower cost in different implementations, for example.

The computing device 34 may be implemented as a single computer, or a combination of multiple computers. For example, the computing device 34 may be a computer server(s) (including a processor(s) and associated memory) located on premises with the enclosed area 32. In other embodiments, such as where IoT sensors are used, a remote or cloud implementation may be used such that the data from the sensors 33a-33n is transmitted to a computing device 34 at a remote location for processing to make the health status determinations. It should be noted that the computing device 34 may also be implemented via a Virtual Desktop Infrastructure (VDI), such as with XENDESKTOP and/or XENAPP from Applicant Citrix Systems, Inc. of Ft. Lauderdale, Fla. (although other suitable systems may also be used). Moreover, as will be discussed further below, other computing devices may be used in conjunction with the system 30, such as mobile computing devices (e.g., smart phones, table computers, etc.) to be carried by staff at the facility to monitor resident or patient health status and receive alerts. Moreover, in some embodiments a non-transitory computer-readable medium may be used having computer-executable instructions to perform the various operations of the computing device 34 described herein.

Figure 3:
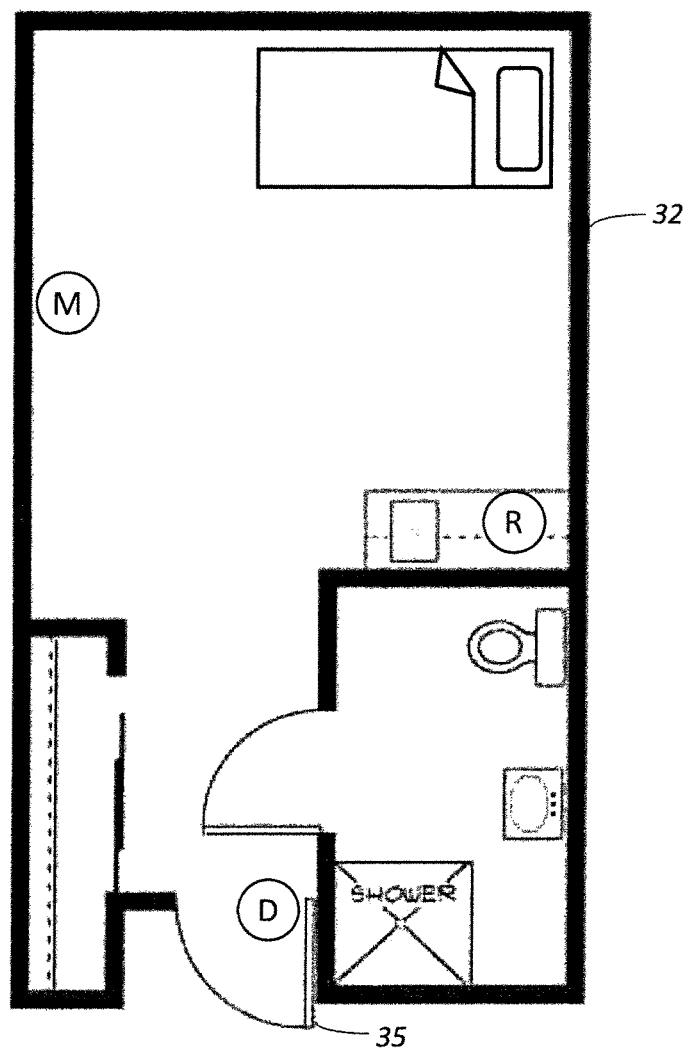
FIG. 3 is a plan view of a room in which the system of FIG. 1 may be used to monitor the health status of a tenant or patient.
Figure 4:
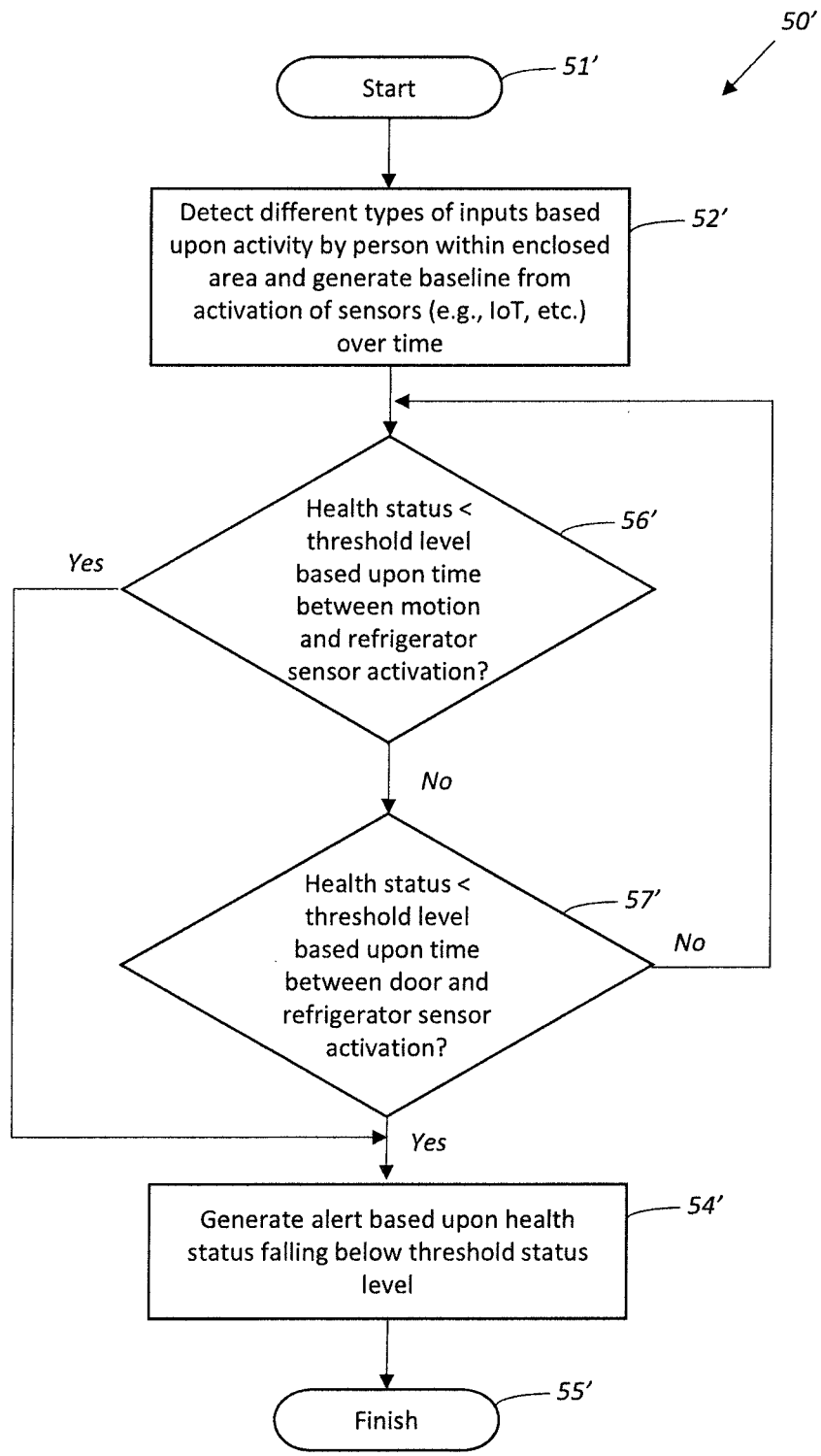

Referring additionally to FIGS. 3-4 and the flow diagram 50' which begins at Block 51', the foregoing will be further understood with reference to an example of a senior citizen living within a room 32 at an assisted living facility. In the illustrated example, there are three different sensors distributed within the room 32, namely a door sensor D which detects when the resident enters and/or exits the room via a door 35, a motion sensor M to detect movement of the resident within the room, and a refrigerator sensor R to detect when the refrigerator is opened by the resident. Example sensor types may include infrared, radar, electrical contact, magnetic, security sensors such as smart card or RFID, laser, photoelectric, temperature, sound/audio, etc.

In the present example, data from the sensors D, M, R is proactively analyzed to generate a baseline and show trending behavior (Block 52'), which may in turn be used for determining patterns that are markers or indicators of a patient's or resident's gradual decline. For example, as patients slip into dementia, they tend to begin missing meals sporadically. Identifying the behavior of missing meals raises awareness to the staff at the assisted living facility that some additional investigation and observation is necessary. The data points collected will grow over time as appliances, monitoring devices, and healthcare devices become "smarter" and more sensors are accordingly connected to the system 30. This may advantageously add to the analytics being used by the computing device 34, which may include machine learning, artificial intelligence (AI), or other suitable framework/architecture to provide the higher-level decision making process that is used for monitoring the tenant. Generally speaking, the machine learning or AI approach used may learn the unique individual patterns of each person being monitored to compare with the declining pattern of activity for determining when the patient's health status has fallen below the given threshold.

In accordance with the present example, the resident's or patient's health status may be determined through various combinations of the sensor input. For example, the computing device 34 may determine that the health status of the senior citizen has fallen below the threshold status level based upon a time between activation of the motion sensor M and a subsequent activation of the refrigerator sensor R, at Block 56'. That is, this may be indicative that the resident is moving about within the room 32 but is not eating at his or her normal times compared to the baseline generated from prior behavior.

In accordance with another example implementation, the computing device 34 may determine that the health status falls below the threshold status level based upon a time between activation of the door sensor D and a subsequent activation of the refrigerator sensor R, at Block 57'. This may be indicative that the resident has been in the apartment for a long period of time without leaving (meaning he or she has not gone elsewhere for food) but is not eating on a normal schedule compared to the baseline generated from prior behavior. One or more of these events (time between motion sensor M and/or door sensor D activation and refrigerator door sensor R activation), as well as other events and other types of sensors, may be used for the health status determination in different embodiments.

In particular, one advantage of the system 30 is that it allows for the use of multiple passive sensors to be used to determine patient or resident health status, which are less intrusive to the person being monitored. For example, in many healthcare environments (e.g., hospitals, etc.), patients have to wear sensors that monitor their vital signs, oxygen levels, etc. While such sensors may also be used in accordance with the system 30, using sensors such as those described above which passively monitor motion or activity of the person within the room 32 without having to be physically connected to the person is much less intrusive for the person.

The system 30 accordingly allows alerts to be proactively sent to staff based on thresholds of motion, refrigerator, and door activity, for example, to alert staff when certain activities have stopped happening for a duration. Thus, the staff have some insight into a potential or developing situation before it becomes critical to the tenant, which otherwise may not be the case if merely relying on routine visits by staff or routine medical checkups of the resident or patient.

The following is an example JavaScript routine which may be used for determining health status changes and generating alerts for the example described above with reference to FIGS. 3 and 4.

```
// Define the notification thresholds in minutes
for ( var room in (msg) ){
    // array to output
    var alertText = [ ];
    // set the default alert level
```

```
        var alertValue = 0; // None = 0, Info = 1, Warn = 2, Critical = 3
        // The alert level should be set to the highest of all possible alerts in the array.
        // minutes between door open and refrigerator open
        if ( msg[room].diffDoorsOpenedMinutes > 1440 ){
            alertValue = 3;
            alertText.push( ( "It has been over " +
moment.duration(msg[room].diffDoorsOpenedMinutes, 'minutes').humanize( ) + " between the door
opening and the refrigerator door opening.") );
        } else if ( msg[room].diffDoorsOpenedMinutes > 960 ){
            if ( alertValue < 2 ) { alertValue = 2 }
            alertText.push( ( "It has been over " +
moment.duration(msg[room].diffDoorsOpenedMinutes, 'minutes').humanize( ) + " between movement
and the refrigerator door has been opened. <b>Please keep an eye out for this tenant.</b>") );
        }
        // minutes between door open and motion
        if ( msg[room].diffDoorMotionMinutes > 120 ){
            if ( alertValue < 1 ) { alertValue = 1 }
            alertText.push( ( "It has been over " +
moment.duration(msg[room].diffDoorMotionMinutes, 'minutes').humanize( ) + " between movement
and the front door being opened.") );
        }
        // minutes between refrigerator open and motion
        if ( msg[room].diffRefrigeratorMotionMinutes > 360 ){
            if ( alertValue < 1 ) { alertValue = 1 }
            alertText.push( ( "It has been over " +
moment.duration(msg[room].diffRefrigeratorMotionMinutes, 'minutes').humanize( ) + " between
movement and the refrigerator has been opened.") );
        }
        // minutes since refrigerator open
        if ( msg[room].sinceRefrigeratorOpenMinutes > 480 ){
            if ( alertValue < 1 ) { alertValue = 1 }
            alertText.push( ( "It has been over " +
moment.duration(msg[room].sinceRefrigeratorOpenMinutes, 'minutes').humanize( ) + " since the
refrigerator door has been opened.") );
        }
        // minutes since door open
        if ( msg[room].sinceDoorOpenMinutes > 1080 ){
            if ( alertValue < 1 ) { alertValue = 1 }
            alertText.push( ( "It has been over " +
moment.duration(msg[room].sinceDoorOpenMinutes, 'minutes').humanize( ) + " since the door has
been opened.") );
        }
        // minutes since motion
        if ( msg[room].sinceMotionMinutes > 480 ){
            if ( alertValue < 1 ) { alertValue = 1 }
            alertText.push( ( "It has been over " +
moment.duration(msg[room].sinceMotionMinutes, 'minutes').humanize( ) + " since movement has been
observed.") );
        }
        if ( alertValue == 3 ) {
            msg[room].alertLevel = "Critical";
            msg[room].bounce = true;
        }
        else if ( alertValue == 2 ) {
            msg[room].alertLevel = "Warning";
            msg[room].bounce = false;
        }
        else if ( alertValue == 1 ) {
            msg[room].alertLevel = "Information";
            msg[room].bounce = false;
        }
        else {
            msg[room].alertLevel = "None";
            msg[room].bounce = false;
        }
        msg[room].alertValue = alertValue;
        msg[room].alertText = alertText;
} // close of for
return msg;
```

Figure 5:
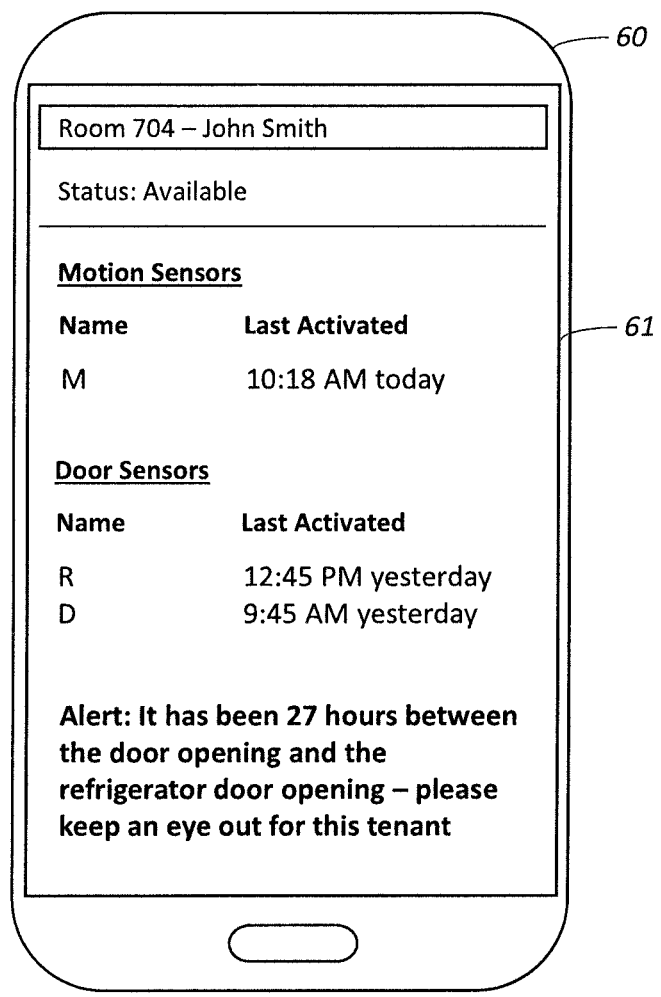
FIG. 5 is a front view of a mobile computing device which may be used with the system of FIG. 1.

Referring additionally to FIG. 5, as noted above, in some embodiments mobile computing may be carried by staff workers to receive alerts from the computing device 34. In the illustrated example, a smartphone 60 with a display 61 runs an app which displays recent sensor data for respective resident rooms 32, as well as alerts for the residents in these rooms when appropriate. In the illustrated example, the status of resident John Smith in Room 704 is shown on the display, along with the latest motion, door and refrigerator sensor inputs. Furthermore, in this example, the above-noted algorithm will have determined that a time of 27 hours has elapsed from when Mr. Smith last returned to his room and the last time he opened his refrigerator. As such, an alert is presented to the smartphone user to keep an eye out for this tenant, so that the staff member can institute additional checkups or actions as necessary. In this example, the sensor tracking/data processing may be performed by the smartphone 60 itself, or by another computing device (e.g., a server) which communicates sensor data alerts to the smartphone.

Various other formats and delivery approaches may be used for sending alerts. For example, the alerts may be sent via text messages, email messages, notifications on the smartphone 60, etc. Moreover, alerts may also be generated on desktop/laptop computers, etc., as well as other mobile computing devices (e.g., tablet computers). Also, it should be noted that while the above-described examples were provided in the context of detecting dementia in an elderly patient in an assisted living facility, the system 30 and associated method aspects described herein may be used for monitoring various other health conditions and declining patient/resident conditions as well. Moreover, it may be used in hospital, home, or other facilities for measuring patient/resident health status.

Many modifications and other embodiments will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included within the scope of the appended claims.

That which is claimed is:

1. A system for monitoring a health status of a person within an enclosed area and comprising:
    a plurality of sensors distributed about the enclosed area, the sensors being configured to detect respective different types of inputs based upon activity by the person within the enclosed area, a first one of the sensors comprising a refrigerator sensor and a second one of the sensors comprising a motion sensor; and
    a computing device cooperating with the sensors to determine an onset of dementia of the person within the enclosed area based upon a timing between activation of the motion sensor and a subsequent activation of the refrigerator sensor indicating a pattern of sporadically missed meals by the person, and generate an alert based upon the determination of the onset of dementia;
    wherein the computing device determines the pattern of missed meals based upon a time difference between the activation of the motion sensor and the subsequent activation of the refrigerator sensor exceeding at least 360 minutes.

2. The system of claim 1 wherein the computing device generates a baseline from activation of the sensors over time, and determines the pattern of sporadically missed meals further based upon the baseline.

3. The system of claim 1 wherein none of the sensors are connected to the person.

4. The system of claim 1 wherein at least one of the sensors comprises an internet of things (IoT) sensor.

5. A method for monitoring a health status of a person within an enclosed area with a computing device and comprising:
    detecting respective different types of inputs based upon activity by the person within the enclosed area from a plurality of sensors distributed about the enclosed area, with a first one of the sensors comprising a refrigerator sensor and a second one of the sensors comprising a motion sensor;
    determining an onset of dementia of the person within the enclosed area based upon a timing between activation of the motion sensor and a subsequent activation of the refrigerator sensor indicating a pattern of sporadically missed meals by the person; and
    generating an alert based upon the determination of the onset of dementia;
    wherein the pattern of missed meals is determined based upon a time difference between the activation of the motion sensor and the subsequent activation of the refrigerator sensor exceeding at least 360 minutes.

6. The method of claim 5 further comprising generating a baseline from activation of the sensors over time, and wherein determining comprises determining the pattern of sporadically missed meals further based upon the baseline.

7. The method of claim 5 wherein none of the sensors are connected to the person.

8. The method of claim 5 wherein at least one of the sensors comprises an internet of things (IoT) sensor.

9. A non-transitory computer-readable medium for a computing device for monitoring a health status of a person within an enclosed area, the non-transitory computer-readable medium having computer-executable instructions for causing the computing device to perform steps comprising:
    detecting respective different types of inputs based upon activity by the person within the enclosed area from a plurality of sensors distributed about the enclosed area, with a first one of the sensors comprising a refrigerator sensor and a second one of the sensors comprising a motion sensor;
    determining an onset of dementia of the person within the enclosed area based upon a timing between activation of the motion sensor and a subsequent activation of the refrigerator sensor indicating a pattern of sporadically missed meals by the person; and
    generating an alert based upon the determination of the onset of dementia;
    wherein the pattern of missed meals is determined based upon a time difference between the activation of the motion sensor and the subsequent activation of the refrigerator sensor exceeding at least 360 minutes.

10. The non-transitory computer-readable medium of claim 9 further having computer-executable instructions for causing the computing device to generate a baseline from activation of the sensors over time; and wherein determining comprises determining the pattern of sporadically missed meals further based upon the baseline.

11. The non-transitory computer-readable medium of claim 9 wherein none of the sensors are connected to the person.

12. A system for monitoring a health status of a person within an enclosed area and comprising:
    a plurality of sensors distributed about the enclosed area, the sensors being configured to detect respective different types of inputs based upon activity by the person within the enclosed area, a first one of the sensors comprising a refrigerator sensor and a second one of the sensors comprising a door sensor; and
    a computing device cooperating with the sensors to determine an onset of dementia of the person within the enclosed area based upon a timing between activation of the door sensor and a subsequent activation of the refrigerator sensor indicating a pattern of sporadically missed meals by the person, and generate an alert based upon the determination of the onset of dementia;

wherein the computing device determines the pattern of missed meals based upon a time difference between the activation of the door sensor and the subsequent activation of the refrigerator sensor exceeding at least 960 minutes.

13. The system of claim 12 wherein the computing device determines the pattern of missed meals based upon a time difference between activation of the door sensor and the subsequent activation of the refrigerator sensor exceeding 1440 minutes.

14. The system of claim 12 wherein the computing device generates a baseline from activation of the sensors over time, and determines the pattern of sporadically missed meals further based upon the baseline.

* * * * *